(12) United States Patent
Martin et al.

(10) Patent No.: US 8,393,198 B2
(45) Date of Patent: Mar. 12, 2013

(54) APPARATUS AND METHOD FOR DETERMINING ANALYTE CONTENT IN A FLUID

(75) Inventors: Tyler P. Martin, Bangor, ME (US); Luke Doucette, Hampden, ME (US); Dean J. Smith, Dover-Foxcroft, ME (US); Thomas P. Schwarz, Orono, ME (US)

(73) Assignee: OronoSpectral Solutions, Inc., Bangor, ME (US)

( * ) Notice: Subject to any disclaimer, the term of this patent is extended or adjusted under 35 U.S.C. 154(b) by 906 days.

(21) Appl. No.: 12/324,688

(22) Filed: Nov. 26, 2008

(65) Prior Publication Data

US 2009/0173145 A1 Jul. 9, 2009

Related U.S. Application Data

(60) Provisional application No. 61/020,063, filed on Jan. 9, 2008, provisional application No. 61/081,620, filed on Jul. 17, 2008.

(51) Int. Cl.
*G01N 33/00* (2006.01)
(52) U.S. Cl. ...................................................... 73/61.41
(58) Field of Classification Search .............. 73/61.41; 356/300–334
See application file for complete search history.

(56) References Cited

U.S. PATENT DOCUMENTS

| 3,612,887 | A | 10/1971 | Canevari et al. | 356/60 |
| 3,967,932 | A | 7/1976 | Sano et al. | 436/73 |
| 3,985,020 | A | 10/1976 | Moreau | 73/61.43 |
| 4,004,453 | A | 1/1977 | Thyrum | 73/61.59 |
| 4,910,406 | A | 3/1990 | Craig et al. | 250/372 |
| 5,109,442 | A | 4/1992 | Klainer et al. | 385/12 |
| 5,244,813 | A | * 9/1993 | Walt et al. | 436/172 |
| 5,268,568 | A | 12/1993 | Lee | 250/214 B |
| 5,470,757 | A | 11/1995 | Gagnon et al. | 436/64 |
| 5,489,988 | A | 2/1996 | Ackley et al. | 356/436 |
| 6,197,598 | B1 | 3/2001 | Schrier et al. | |
| 6,212,939 | B1 * | 4/2001 | Thundat | 73/24.02 |
| 6,489,132 | B1 | 12/2002 | Gordon et al. | |
| 6,562,309 | B2 | 5/2003 | Burke et al. | 423/245.1 |
| 6,717,658 | B1 | 4/2004 | Saini et al. | 356/70 |

(Continued)

FOREIGN PATENT DOCUMENTS

| DE | 2754293 | 6/1978 |
| EP | 0926484 | 6/1999 |

(Continued)

OTHER PUBLICATIONS

Romero, M. Teresa and Ferrer, Nuria, Determination of oil and grease by solid phase extraction and infrared spectroscopy, Analytica Chimica Acta, 1999, 77-84, 395, Elsevier.

(Continued)

*Primary Examiner* — Peter Macchiarolo
*Assistant Examiner* — Tamiko Bellamy
(74) *Attorney, Agent, or Firm* — Verrill Dana, LLP; Chris A. Caseiro

(57) ABSTRACT

An apparatus and method to determine analytes in a fluid. One aspect of the present invention is for the determination of the oil content of water using UV, near-IR, IR or Raman spectroscopy or radiometry. In certain embodiments, a solid membrane material absorbs analytes from fluid brought into contact with it. The membrane is subsequently placed in a FTIR spectrometer, which spectrometer is enabled to determine the concentration of analytes in fluid by calibration. Certain embodiments can determine the type of hydrocarbon present, and thus can differentiate Total Petroleum Hydrocarbons (TPH) from Total Oil and Grease (TOG), without any separate sample preparation.

26 Claims, 11 Drawing Sheets

U.S. PATENT DOCUMENTS

| | | | |
|---|---|---|---|
| 6,953,550 B2 | 10/2005 | Sheppard, Jr. et al. | 422/63 |
| 2003/0231304 A1* | 12/2003 | Chan et al. | 356/301 |
| 2004/0115822 A1 | 6/2004 | Schapaugh et al. | |
| 2005/0129925 A1 | 6/2005 | Klare et al. | 428/319.3 |
| 2005/0175501 A1 | 8/2005 | Thompson et al. | |
| 2005/0254995 A1 | 11/2005 | Sostek et al. | 422/400 |
| 2008/0192246 A1* | 8/2008 | Neiss et al. | 356/301 |
| 2011/0097814 A1* | 4/2011 | Bommarito et al. | 436/164 |

FOREIGN PATENT DOCUMENTS

| | | |
|---|---|---|
| EP | 1211505 | 6/2002 |
| EP | 1500930 | 1/2005 |
| JP | S49-016494 | 2/1974 |
| JP | S55-156838 | 12/1980 |
| JP | 10-508699 | 8/1998 |
| JP | 2001-296240 | 10/2001 |
| WO | WO 9418559 A1 * | 8/1994 |
| WO | WO96/14563 | 5/1996 |

OTHER PUBLICATIONS

International Search Report and Written Opinion for corresponding PCT application No. PCT/US2009/030069, 7 pp.
Extended Supplementary Search Report in corresponding European application 09701432.8, European Patent Office, Nov. 22, 2011, 6 pp.
Notification of Reasons of Refusal in corresponding Japanese application No. 2010-542296 (with translation), Mar. 12, 2012, 4 pp.
Update to Notification of Reasons of Refusal in corresponding Japanese application No. 2010-542296 with complete translation of the Reasons for Refusal, Mar. 12, 2012, 3 pp.

* cited by examiner

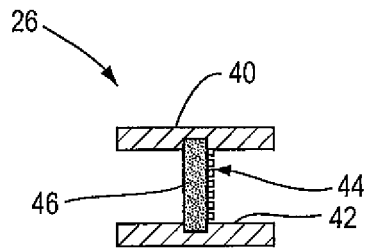 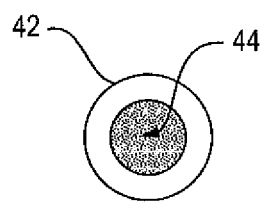 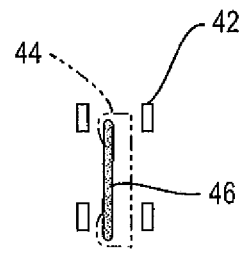
FIG. 3　　　　　FIG. 4　　　　　FIG. 5
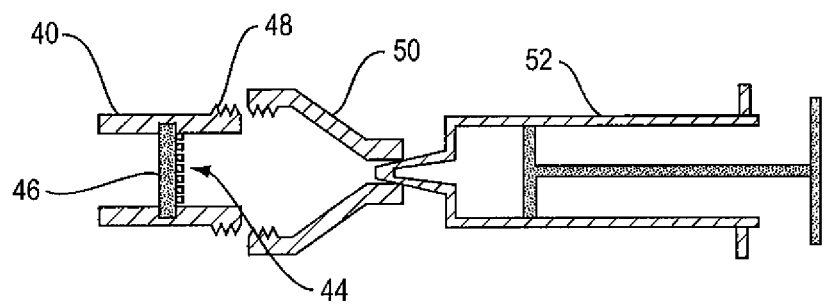
FIG. 6
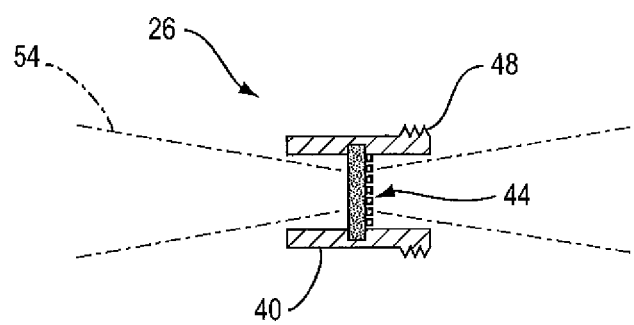
FIG. 7

| SOURCE | RUN 1 | RUN 2 | RUN 3 | EPA 1664* |
|---|---|---|---|---|
| GULF A | 4 | 4 | 6 | 4** |
| GULF B | 13 | 17 | 15 | 10 |
| FOOD PROCESSOR | 108 | 108 | 83 | 96 |
| PRISON | 46 | 39 | 48 | 49 |
| PAPER MILL | 10 | 8 | 12 | 12 |
| MUNICIPAL WASTE WATER - PRIMARY EFFLUENT | 24 | 18 | 18 | 17 |

*EPA 1664 Performed by Katahdin Analytical Laboratories, Scarborough, ME
** Technically below the EPA 1664 lower reportable limit.

FIG. 23

APPARATUS AND METHOD FOR DETERMINING ANALYTE CONTENT IN A FLUID

CROSS REFERENCE TO RELATED APPLICATIONS

The present application claims the priority benefit of U.S. provisional application Ser. No. 61/020,063 filed Jan. 9, 2008, entitled SOLVENTLESS APPARATUS AND METHOD FOR DETERMINING HYDROCARBON CONTENT IN WATER, of the same named inventors, and U.S. provisional application Ser. No. 61/081,620 filed Jul. 17, 2008, entitled SOLVENTLESS APPARATUS AND METHOD FOR DETERMINING HYDROCARBON CONTENT IN WATER AND RELATED ANALYSES, of the same named inventors. The entire contents of both priority applications are incorporated herein by reference.

STATEMENT REGARDING FEDERALLY SPONSORED RESEARCH OR DEVELOPMENT

This invention was made using funds obtained from the US Government (US Army, Contract No. W911SR-06-C-0035), and the US Government therefore has certain rights in this invention.

BACKGROUND OF THE INVENTION

1. Field of the Invention

The present invention relates to devices and techniques used to determine the analyte content in a fluid. More particularly, the present invention relates to systems and methods for capturing analytes on a test bed for subsequent analysis in a test device. The present invention is related, but not limited to, devices and methods for determining hydrocarbon content in water.

2. Description of the Prior Art

There is a need for a new fast and economical hydrocarbon in water measurement technique that directly measures the oil content of water and does not require the use of any solvents. Infrared absorption measurements have been the preferred basis of measurement for over twenty years. However, these measurements require first performing a liquid-liquid extraction to remove the hydrocarbon from the water. The preferred solvents for performing the extraction, such as Freon, S-316, and perchloroethylene have been banned or are being phased out due to environmental, health, and safety concerns. The sensing and detection industry response to this challenge has been to introduce new methods and instruments not based on IR absorption.

As used herein, "hydrocarbon" means all molecules containing hydrogen and carbon; examples include aliphatic and aromatic molecules as well as carboxyl groups in carboxylic acids or ester groups. As used herein, "oil" means a mixture of aliphatic hydrocarbons with generally between seven and 40 carbons in the chain, aromatic species, and other hydrocarbons. It includes crude oil, refined oil, heating oil, and any other form of carbon-based oil.

The current method approved by the Oslo-Paris Convention (OSPAR) for use in Europe and Scandinavia is Gas Chromatography-Flame Ionization Detection (GC-FID) (OSPAR Commission Reference Number 2005-15). The method requires the use of solvent (pentane is recommended) to perform a liquid-liquid extraction for sample preparation. This method has the advantage of directly measuring the oil content and differentiating TPH from BTEX and Grease. However, GC-FID is extremely time consuming and labor intensive, requiring up to an estimated 6 hrs per measurement and many more for periodic recalibrations. Also, the differentiation of TPH from Grease content is not inherent in the measurement technique but instead requires separate sample preparation by an experienced operator. By contrast, the present invention does not require the use of solvents, requires as little as a few minutes per measurement with no sample preparation with little or no recalibration, and does not require separate sample preparation to determine TPH and Grease content in certain embodiments.

As used herein, "TPH" means Total Petroleum Hydrocarbons, generally including non-volatile aliphatic molecules of varying chemical structure with up to 40 carbons. As used herein, "BTEX" stands for all aromatic organic molecules, including Benzene, Toluene, Ethylbenzene, and ortho-, meta- and para-Xylene. As used herein, "Grease" refers to long chain hydrocarbon molecules containing carboxylic acid and/or ester functional group or groups.

The current US standard method approved by the Environmental Protection Agency ("EPA") (EPA 1664) to replace the previous IR-based methods (EPA 418.1 and 413.2) is also based on liquid-liquid extraction. Simply, after extracting the oil from the water into a solvent, generally hexane, the hexane is evaporated and total mass of material remaining is measured and reported as the TPH or TOG (as used herein, "TOG" means Total Oil and Grease; that is, the total of TPH and Grease and excluding BTEX). The EPA 1664 method also introduced new terminology specific to the method. Instead of TOG, EPA 1664 refers to Hexane Extractable Material, or HEM. Instead of TPH, EPA 1664 refers to Silica Gel Treated Hexane Extractable Material, or SGT-HEM. Differentiating TOG (or HEM) from TPH (or SGT-HEM) requires separate sample preparation by the operator. This method is also labor intensive and the measurement takes a long time. It must be ensured that there is no water present and all the hexane is evaporated, as the presence of either will result in over-reporting the TPHl/TOG content of the sample. This means one measurement can take up to 48 hrs. In a revision to EPA 1664, the EPA has promulgated EPA 1664A, a technique that allows solid phase extraction (SPE) of the HEM from water using SPE discs or cartridges, followed by the elution of the HEM from the SPE material with hexane. As in EPA 1664, the hexane is then evaporated from the sample and the remaining material is weighed to determine HEM. SGT-HEM is determined by re-dissolving the HEM in hexane to perform the silica gel treatment. While EPA 1664A reduces the amount of solvent required and the time to perform the test, it cannot be used on certain samples due to clogging issues and does still require significant solvent use (about 200 ml of hexane per test) and time (about 1.5 hrs for most samples). Again, the present invention requires very little processing time per measurement, does not require separate sample preparation to determine TPH and Grease content in certain embodiments, and does not require solvents.

Other competing measurement techniques are based on the ultraviolet fluorescence, ultraviolet absorbance, or simultaneous spectral ultraviolet fluorescence/absorbance of the BTEX components of the oil content. They have the advantage of being capable of measuring very low amounts (as low as 50 ppb has been claimed) of BTEX in water and measuring the sample in water with no liquid-liquid extraction sample preparation step. However, since this method is based on measuring just the aromatic (BTEX) component of the sample, the presence of TPH and/or Grease must be determined by calibration of the expected oil stream by some method that can measure all three components. This issue is a significant drawback when performing measurements for regulatory compliance, which generally require the measurement of all the polluting components of the aqueous sample of interest, and when unknown oil contaminant streams are encountered.

Light scattering/turbidity is the other major non-IR based technique in use for oil in water analysis. This technique relies on the fact that oil is very slightly soluble in water (generally below 1 ppm) and so it is actually a two-phase system, i.e., oil is present as droplets in water. These droplets scatter light of certain wavelength depending on the droplet size and the intensity of the scattering at a certain wavelength depends on both the number of droplets and droplet size. Therefore, the number and size of oil droplets can be measured by examining the light scattering profile of the flowing two phase fluid system. However, problems are encountered with gas bubbles and solid particles also scattering light, thus leading to overestimating the oil content of the sample. The walls of such a device must be transparent to the wavelength range of interest at the point the measurement is performed. However, oil and other potential contaminates in the sample will tend to rapidly foul all surfaces, necessitating thorough cleaning after relatively short periods of operation.

Other methods, such as those based on ultrasonic acoustic pulse echo, are unproven and highly complex and thus unlikely to find wide acceptance.

German Patent No. DE2754293 describes a particular extraction solvent for use in automated systems available from HORIBA, Ltd, of 2 Miyanohigashi, Kisshoin, Minami-ku Kyoto 601-8510 Japan. These systems were designed for use to comply with EPA 418.1, and so are essentially made obsolete by the banning or phasing out of most extraction solvents. While these systems use the infrared radiation absorbing property of hydrocarbons as the basis for sensing oil in water, they require the use of solvent for liquid-liquid extraction.

The standard practice worldwide generally required the use of chlorofluorocarbon solvents, which are harmful to the ozone layer and have generally been banned worldwide, or other extraction solvents, such as perchloroethylene, which are hazardous to the health and safety of the operator and are also being phased out worldwide. Therefore, the solvent-based systems are generally obsolete in practice. Some other systems provide for the capture and regeneration of the extraction solvent for reuse, but this is generally considered insufficient environmentally.

U.S. Pat. No. 5,109,442 describes a hydrophobic material such as Teflon® (available from the Dupont Company of Delaware) that is used solely as a waterproofing component and not as a hydrocarbon-absorbing material as in the present invention, but the use of that system containing Teflon® material for oil in water measurement is not described. In general, the absorptive film consists of a metal having a refractive index that changes when in contact with various analytes. This metal film is coated on an optical fiber through which light of some unknown frequency is passed, but which cannot be infrared radiation due to the fiber optic material. The change in refractive index of the cladding results in a change in the light signal exiting the optical fiber which is correlated to the concentration of analyte in the gas or liquid being measured. Therefore, this technique does not directly measure the oil content, but instead measures a change in a secondary material property (refractive index) of the cladding. Also, it is explicitly stated that platinum cladding responds strongly to the BTEX components, so in effect the sensing methodology is twice removed from directly measuring the oil content. That is, the device is measuring a secondary material property response to only a small portion of the total hydrocarbon content in the water. The technique therefore relies on calibrations of the total hydrocarbon content relative to the content of BTEX compounds which is often unknown and or changing with time.

In "Determination of oil and grease by sold phase extraction and infrared spectroscopy", Analytica Chimica Acta 395 (1999) 77-84), Ferrer and Romero describe a method which requires a vacuum filtration apparatus to perform the oil separation from water. A vacuum filtration method fails to supply sufficient pressures to ensure fluid flow in a timely manner (i.e. <10 minutes) through a membrane due to filter clogging. This limitation is significant since real-world samples typically contain high levels of metals/metal oxide particles, organic materials, and other paticulates which clog and consequently inhibit fluid flow though the membrane unless sufficiently high differential pressures across the membrane are applied.

The Romero method further requires the membrane to be physically handled and extracted from the vacuum filtration apparatus, then re-attached to a different membrane holder via magnetic supports for post-collection IR analysis. Among other things, this can lead to undesirable collector contamination and delays in the analysis process. These and other limitations of the Romero method as described in the noted reference result in a system that is not adequate for commercialization.

Ferrer and Romero further describe another system for the determination of hydrocarbons in water in "Fourier Transform Infrared Spectroscopy and Solid Phase Extraction Applied to the Determination of Oil and Grease in Water Matrices," Microchemica Acta 140, 35-39(2002), which consists of a vaporizing hydrocarbons out of the water sample and onto a PTFE disc suspended above the water surface. The method is recommended by the authors mainly for use on diesel and petrol-containing samples, as the processing conditions (heat and time, up to 14 hours in some cases) and calibration to be used vary considerably with the type of hydrocarbon present in the water sample. The described method thus is not widely applicable or commercially viable.

While the description of the prior art has been directed to the determination of hydrocarbon content in water, it is to be noted more generally that there is a need for a commercially suitable apparatus and related method to detect analytes in fluids with reasonable accuracy. In general, it is desirable to have an analyte determination apparatus and method that effectively retains accurate and reliable samples of the analyte for evaluation using known evaluation tools including, but not limited to, IR spectroscopy.

SUMMARY OF THE INVENTION

It is an object of the present invention to provide a commercially suitable apparatus and related method to detect analytes in fluids. It is also an object of the present invention to provide an apparatus and method for analyte determination that effectively retains accurate and reliable samples of the analyte for evaluation using known evaluation tools.

These and other objects are achieved with the present invention, which is an apparatus and related method for analyte determination. The apparatus includes a fixture with an analyte-retaining membrane selected for minimal or no interaction with the analyte or analytes of interest. In certain embodiments, the membrane material is configured as part of the test fixture in a manner that ensures it will absorb or otherwise capture the analyte of interest from fluid brought into contact with it. The membrane either alone or in a portion or all of the test fixture, is subsequently placed in a spectrometer, radiometer or other detection tool and processed. The content and concentration of analytes retained on the membrane are then calculated using analysis software, for example.

The apparatus of the present invention includes a sampling device, an optional sample pre-treatment subsystem, a sample preparation subsystem, a sample collection subsystem, an optional collected sample pretreatment subsystem, a sample delivery subsystem, an analyte retention device (which includes the membrane described), an optional sample collection and retention device flushing subsystem, a drying subsystem, an analysis subsystem and an optional data archiving subsystem.

The membrane contains minimal or no amount of the analyte of interest or minimal amounts or zero chemical bonds similar to the chemical bonds in the analyte of interest, which bonds may interfere with the wavelength detection range or ranges of interest. If the membrane contains the analyte or chemical bonds similar to the analyte, it must be such that they can be accounted for in the analysis of the tested membrane. For the purpose of determining hydrocarbon content in water, for example, the membrane contains minimal or zero hydrocarbon bonds which interfere with the wavelength detection range or ranges of interest. In this particular example, the membrane may be used to determine the type of hydrocarbon molecule present, and thus can differentiate TPH from TOG, without any separate sample preparation.

It is to be understood that while an emphasis of the disclosure of the present invention is directed to the detection of hydrocarbons in water, it is to be understood that the features and attributes of the invention may be used to aid in the detection of analytes generally and in other fluids including, but not limited to, air.

The present invention is an analyte determination apparatus and related method having the following characteristics: 1) accuracy; 2) minimal processing time to minimize sample compromise due to separation, oxidation, etc.; 3) a system designed to minimize sample degradation and contamination, for example; 4) ability to handle real world particulates, biologics, metals, salts and other interferents; 5) scalable for automation—system components can be designed and packaged to support on-line and/or off-line automated sampling and analyses; 6) ability to handle a wide dynamic range of analytes—the apparatus operates on the principle of mass loading, as a result, variable sample volumes can be accurately passed through it; and 7) efficient extraction to capture the analyte of interest.

These and other features and advantages of the present invention will become apparent upon review of the following detailed description, the accompanying drawings and the appended claims.

BRIEF DESCRIPTION OF THE DRAWINGS

FIG. 3 is a cross sectional side view of a first embodiment of the analyte retention device of the present invention.

FIG. 4 is a plan view of the membrane and seal of the retention device of the present invention.

FIG. 5 is a cross sectional side view of the membrane, seal and support of the retention device.

FIG. 6 is a cross sectional side view of an embodiment of the retention device joined to a flow expander.

FIG. 7 is a cross sectional side view of the retention device of FIG. 6 with the membrane shown subjected to an IR beam.

FIG. 23 is a table representing the results of experiments conducted on six real-world fluid samples using the present invention in comparison to a standardized solvent-based analysis of produced water from crude oil production platforms in the Gulf of Mexico.

DETAILED DESCRIPTIONS OF THE PREFERRED EMBODIMENTS OF THE INVENTION

In general, the present invention relates to the determination of analytes in fluids. More specifically, an example of the present invention is directed to the determination of hydrocarbons in water. Hydrocarbons in water are known to be harmful to the environment and human health. 'Water' can indicate fresh water, sea water, municipal waste water, petroleum industry produced water (as used herein, "produced water" means waste water produced, for example, in crude oil pumping or during industrial processing), bilge water from ships, and other waters. Each source of water has a limit to the concentration of hydrocarbons that can be present before the water can be discharged to the environment. Regulatory agencies worldwide enforce these limits by requiring periodic testing at industrial sites and others where hydrocarbons may be present in the water. The present invention seeks to provide an accurate, economical, rapid, environmentally-friendly solution to the problem of measuring hydrocarbons in water.

Figure 1:
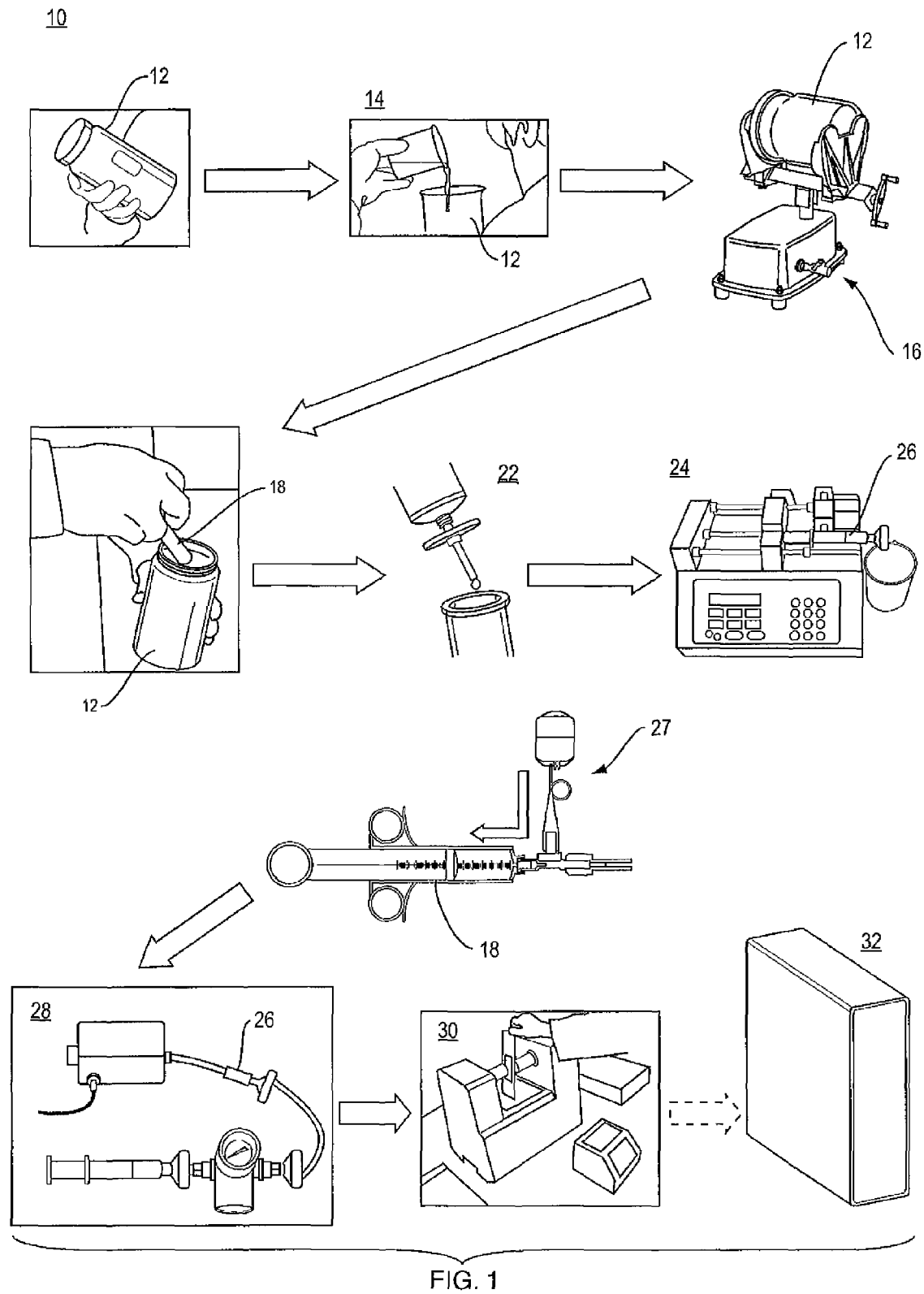
FIG. 1 depicts a simplified representation of the primary subsystems of the apparatus of the present invention.

As illustrated in FIG. 1, an analysis apparatus 10 of the present invention includes a sampling device 12, an optional sample pre-treatment subsystem 14, a sample preparation subsystem 16, a sample collection subsystem 18, an optional collected sample pretreatment subsystem 22, a sample delivery subsystem 24, an analyte retention device 26, an optional sample collection and retention device flushing system 27, a drying subsystem 28, an analysis subsystem 30 and an optional data archiving subsystem 32.

The sampling device 12 is used to retrieve a fluid to be analyzed for one or more analytes of interest. The sampling device 12 is selected to conform to regulatory requirements for containers suitable to retain therein a batch of a fluid to be analyzed. The sample device 12 should be fabricated of an inert material, i.e., something that is non-extractable and that yields no or minimal loss/degradation of analyte during storage and any travel. The sampling device 12 may be selected for suitability in an automated operation of a portion or all of the analysis apparatus 10. A glass container with sealable cap is a suitable sampling device, provided it includes a port sufficiently sized to receive the fluid under analysis coming from a source of known characteristics, such as a faucet, a pond or a conduit, for example. A one-liter glass beaker with a Teflon®-lined cap has been found to be suitable as the sampling device.

The optional sample pre-treatment subsystem 14 is used to condition the sample, if deemed suitable, prior to transfer to the analyte retention device 26. Such pretreatment may be necessary, for example, when a significant period of time may pass between sampling and processing in order to preserve the sample; or to condition the sample in preparation for processing. It is selected as a tool or a method that is arranged to conform to standard and/or regulatory requirements, such as pre-treatment to acidify the fluid, for example. The optional sample pre-treatment may be conducted in the sampling device 12 or another suitable container having characteristics conforming with the characteristics of the sampling device 12. The optional sample pre-treatment subsystem 14 is selected to ensure that it does not effect or impact the detection of the analyte in the fluid. The optional sample pre-treatment subsystem 14 may be selected for suitability in an automated operation of a portion or all of the analysis apparatus 10.

The sample preparation subsystem 16 includes one or more tools suitable for preparing the gathered sample for analysis. The sample preparation subsystem 16 is arranged to effectively agitate the sample to ensure homogeneous sample prior to transfer to the sample collection subsystem 18. The sample preparation may be performed such as by manual shaking, automated shaking, using a laboratory mixer, magnetic stirring, ultrasonic mixing or a combination thereof. An example of a suitable automated shaker is the Model 94605 shaker made available by Central Pneumatic Paint Shaker of Camarillo, Calif. An example of a suitable laboratory mixer is the Stirring Hotplate made available by Cole Parmer Thermo Scientific of Vernon Hills, Ill. An example of a suitable ultrasonic mixer, which breaks up particles, is the IKA Ultra-TulTax T-18 Homogenizer made available by Daigger of Vernon Hills, Ill. The sample preparation subsystem 16 selected may be operated based on suitable time and technique characteristics that ensure homogenization of the sample. The sample preparation subsystem 16 may be selected for suitability in an automated operation of a portion or all of the analysis system.

The sample collection subsystem 18 is used to remove a selectable volume of the fluid under analysis from the sampling device 12 for transfer to the analyte retention device 26. It is selected to have at least the following characteristics. It must be able to effectively draw, house, and deliver sample under test. It could be traceable to a delivery accuracy standard, such as NIST and/or ISO manufacturing standards. It should effectively handle wide pressure range and positive pressures. It is selected so that it does not introduce oil, grease, other any other analyte interferents. It is preferably disposable and/or retained in sterile sealed containment, but need not be. It is a closed system so as to eliminate or minimize the possibility of introducing external contamination into the analysis process. It could have a standardized coupling interface, such as a standard connection, for example, a LUER interface. The sample collection subsystem 18 is inert and made of a material that is non-extractable; that is, a material that will not leach into the fluid stream during the analysis method process.

The sample collection subsystem 18 is selected to enable smooth sample drawing with a positive safety stop to prevent accidental spills. It should be accurate, with easy-to-read fine increments for sample transfer with precision. The sample collection subsystem 18 is preferably arranged to be capable of being adapted to the optional sample collection and retention device flushing subsystem 27 to 'flush' any remaining analyte through the system, including the retention device 26, as desired. It is also preferably arranged for adaptation to the optional sample pretreatment subsystem 22 in order to filter out potential interferents and/or treat the sample to optimize analysis. Finally, the sample collection subsystem 18 may be selected for suitability in an automated operation of a portion or all of the analysis apparatus 10. The nonpyrogenic, nontoxic, sterile Norm-Ject LUER Lok syringe available from Henke Sass Wolf of Tuttlingen, Germany is a suitable embodiment of the sample collection subsystem 18.

The optional collected sample pretreatment subsystem 22 may be used to condition the fluid just prior to transfer to the retention device 26, such as by filtering out any interferents that may adversely impact the analysis method. It is selected to have at least the following characteristics. It filters out any extraneous material that may have been introduced in the acquisition of the original sample batch or introduced via any of the upstream subsystems. It is preferably arranged to be compatible with at least the sample collection subsystem 18, the sample delivery subsystem 24, and the analyte retention device 26. It is capable of filtering out chemical and/or physical interferent materials (e.g. palticulate matter) without compromising analyte, data quality, or system accuracy. It is selected so as not to introduce interferents to the fluid under analysis. It may retain a low volume of the fluid treated so as to maximize the sample volume presented to the analyte retention device.

The optional sample pretreatment subsystem 22 is preferably disposable and/or retained in sterile seated containment, but need not be. It is a closed system so as to eliminate or minimize the possibility of introducing external contamination into the analysis process. Finally, the sample pretreatment subsystem 22 may be selected for suitability in an automated operation of a portion or all of the analysis apparatus 10. The sample pretreatment subsystem 22 may be formed by a combination of a Millipore syringe filter, Millex-HV/PB filter unit, both available from Millipore Corporation of Billerica, Mass., and a chemically-inert filter material such as, but not limited to glass fibers, for example.

The sample delivery subsystem 24 is used to physically transfer prepared sample from collection/pretreatment to the analyte retention device 26. It is selected and arranged to include at least the following characteristics. It is capable of providing optimal differential pressure through the sample collection subsystem 18, the optional sample pretreatment subsystem 22, and the analyte retention device 26 without compromising materials or results. It may either provide manual or automated delivery of the sample. In the manual form, the sample delivery subsystem 24 may simply be the piston of the syringe of the sample collection subsystem 18 actuated by hand, or it may be a modified adhesive gun. Manual delivery may or may not include a feedback mechanism to characterize flow rate and pressure. In the automated form, the sample delivery subsystem 24 may be a syringe pump, such as the Remote Infuse/Withdraw PHD 22/2000 syringe pump made available by Harvard Apparatus of Holliston, Mass. Alternatively, it may be a modified power adhesive gun. The automated tool may or may not include feedback control of pressure and/or flow rate—depending on application requirements. The automated delivery embodiment is preferable in that it is more likely to provide accurate controlled delivery (e.g. total volume, flow rate profile and pressure profile).

The sample delivery subsystem 24 is preferably selected so that it does not introduce any contaminants or analyte interferents into the process. It may be adapted to provide sample agitation if necessary to assist in moving particulate-laden samples through the system. For example, in the automated form, it may include vibrational shaking, such as with an off-balance motor, or acoustic pulsing, such as with a sonic energy pen. The sample delivery subsystem 24 may be selected for suitability in an automated operation of a portion or all of the analysis apparatus 10.

The analyte retention device 26 described in greater detail herein, is configured to retain analytes contained in the fluid under analysis that has been collected. The retention device 26 includes at least the following characteristics. It is a single component device with no moving parts and requires minimal or no manipulation to get the retained analytes therefrom to the analysis subsystem 30. It can handle wide differential pressure ranges (and thus a wide range of flow rates), including non-constant pressure fluid flows, e.g., constant flow rates, including positive pressures exceeding 100 psi. It is readily adaptable to IR spectrometry in that it provides an optimized analysis area for IR spectrometry, i.e., throughput match. It is capable of working with appropriate sample volume ranges based on the particular application of interest. The retention device 26 is a closed system so as to eliminate or minimize the possibility of introducing external contamination into the analysis process. The retention device 26 is fabricated of one or more inert and non-extractable materials; that is, a material(s) that will not leach into the fluid stream during the analysis process. The retention device 26 may be selected for suitability in an automated operation of a portion or all of the analysis apparatus 10.

Figure 2:
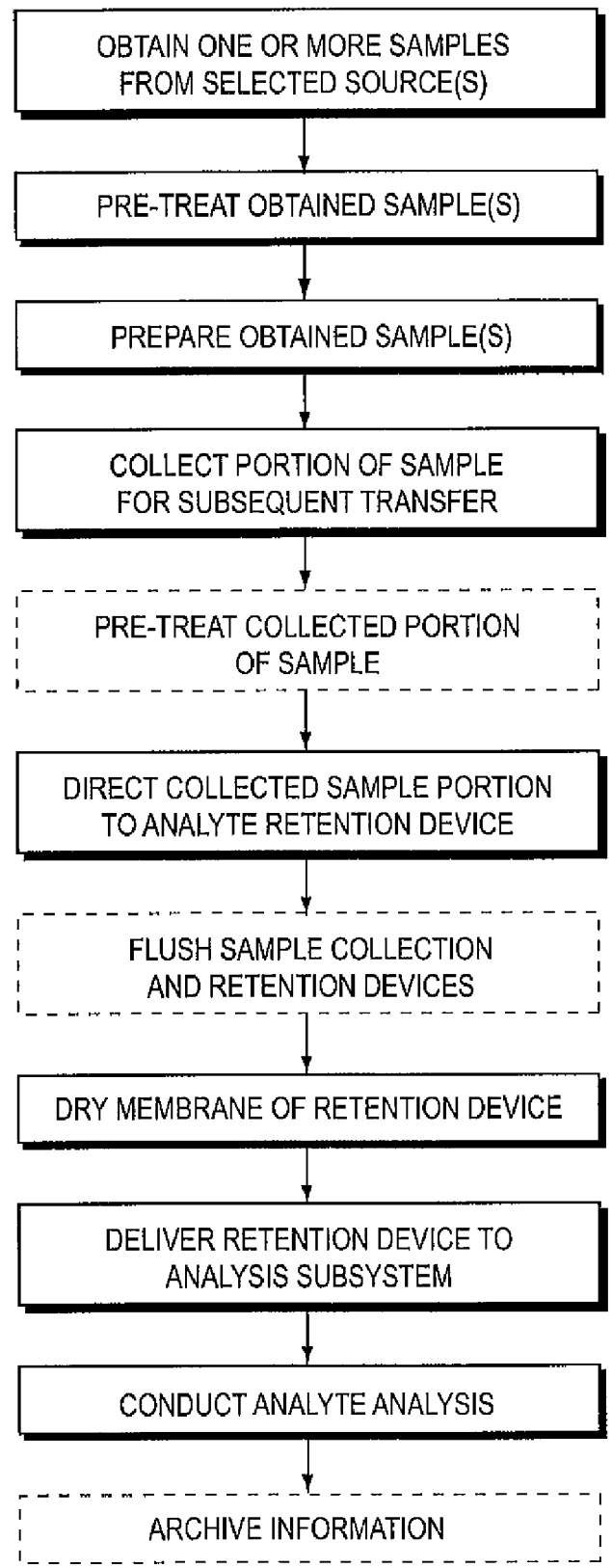
FIG. 2 depicts a simplified representation of the analysis method of the present invention.

As illustrated in FIG. 2, an analysis method 100 of the present invention includes a plurality of steps, one or more of which may be optional steps, for obtaining and preparing a sample of a fluid that may include one or more analytes to be determined, and the steps associated with making that determination. The first step of the method involves obtaining a sample of the fluid from one or more selected sources. Next, the obtained sample may optionally be pretreated as described herein. The sample, whether pre-treated or not, is then prepared for collection. That step of preparation has also been described herein. At least a portion of the prepared sample is then transferred to the sample collection subsystem for collection. Next, the collected sample may optionally be pretreated, also as previously described. The collected sample, whether pretreated, is transferred to the analyte retention device 26 in a manner that results in the fluid passing over or through a membrane to be described herein. The sample collection subsystem 18 and the retention device 26 are optionally flushed using the flushing subsystem 27, described herein. The retention device 26, whether flushed or not, is then dried in the drying subsystem 28 and transferred to the analysis subsystem 30, where it is then subjected to testing for the purpose of analyte detection. The information associated with the analysis may then be used to perform calculations known to those of ordinary skill in the art. The apparatus 10 and the method 100 of the present invention are directed to an improved sample collection arrangement so that the most effective sample is supplied to the analysis subsystem 30. The resultant calculations performed, any sample information and/or analysis information may optionally be reported and/or archived in archiving subsystem 32.

As illustrated in FIGS. 3-5, the analyte retention device 26 includes a housing 40, a seal 42, a membrane 44, and a support 46, all to be described in greater detail herein with respect to specific embodiments depicted in a portion of the figures. In general, it is noted that the housing 40 may have a standard connection, e.g., LUER. It may be fabricated in an array of various designs optimized to meet specific application (size, materials, flow rate, flow volumes, pressure) requirements. The seal 42 defines and establishes a reproducible flow area. That is, it establishes a consistent sample flow area, which flow area may be equivalent to an IR beam path cross section, for example. The seal 42 seals the perimeter of the membrane 44 and the support 46 so as not to allow analyte or interferent material to flow around/under the membrane 44 into the analysis field. More generally, the seal 42 provides an air and liquid tight seal. The material chosen for the seal 42 is selected to be physically and chemically robust enough to handle differential pressures across the membrane 44 and the support 46 without compromising materials or analysis. It is also selected not to affect the IR processing of the sample.

In general, the membrane 44 of the analyte retention device 26 is selected for optimally capturing analytes of interest as described herein. The support 46 is, effectively, a neutral density component and is configured to provide rigidity to the membrane 44. The support 46 is configured so as to not block fluid flow through or across the membrane 44. It is selected to be amenable for IR spectrometry of the analyte of interest, and is capable of standing up to differential pressures across the membrane 44 without compromising the integrity of the other components of the retention device 26.

The support 46 functions as a structural support for the membrane 44. The membrane 44 is porous and effectively acts to distribute the fluid under analysis to pass therethrough or thereover. Similarly, the support 46 is configured to aid, or at least not to disrupt, the homogeneity of the fluid cross section passing through or over the membrane 44. For example, the support 46 may also be porous. Its porosity may be the same as or different from the porosity of the membrane 44. That porosity of the support 46 may be selected as a function of the size of the area of the membrane 44 that is actually subject to the analysis. When the entire surface of the membrane 44 is subject to analysis (i.e., the beam path of IR spectroscopy substantially matches the area of the membrane 44), the support 46 may have relatively large pores, as long as it provides support for the membrane 44. When only a portion of the surface of the membrane 44 is subject to analysis (i.e., the beam path of IR spectroscopy is less than the area of the membrane 44), the support 46 should have relatively smaller pores so as to aid in distributing the fluid uniformly through or across the membrane 44.

The support 46 may be a separate component of the retention device 26 that fits within the housing 40. In that case, the membrane 44 and the support 46 may together be removed from the housing 40 and inserted in the test fixture. Alternatively, the support 46 may be formed as a permanent integral part of the housing 40 and only the membrane 44 may be removed from the housing 40 and inserted into the test fixture. In another embodiment of the invention, the entire housing 40, containing the membrane 44 or the membrane 44 and support 46, may be inserted in the test fixture. It is also to be noted that one or more components of the retention device 26, including the housing 40, the support 46, or both, may be reuseable.

In an embodiment of the invention represented in FIGS. 6 and 7, the housing 40 includes external threading 48 suitable for removable coupling of the retention device 26 to another device, such as flow expander 50. The flow expander 50 may be used to distribute collected sample across the surface of the membrane 44, such as when the sample delivery subsystem 24 includes a syringe 52 that would otherwise direct a relatively narrow flow stream to the membrane 44. In this embodiment, the retention device 26 may be removed from the expander 50 by unthreading or other means, and the entire retention device 26 may be inserted into the analysis subsystem 30 for analysis. FIG. 7 illustrates the complete retention device 26 with an IR beam 54 of an IR spectrometer directed to the membrane 44.

Figure 8:
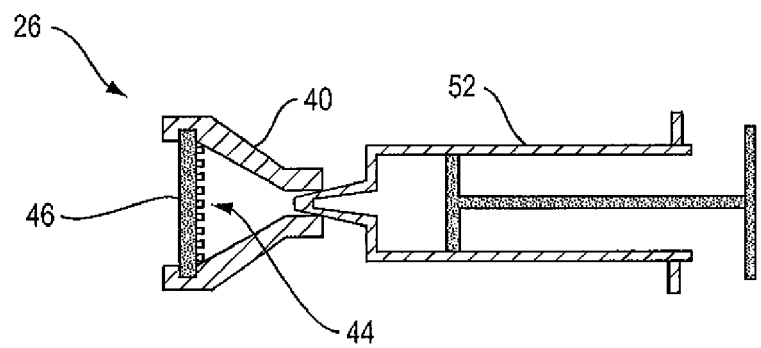
FIG. 8 is a cross sectional view of a first alternative embodiment of the retention device of FIG. 6 that does not require any manipulation prior to drying, flushing or measurement.
Figure 9:
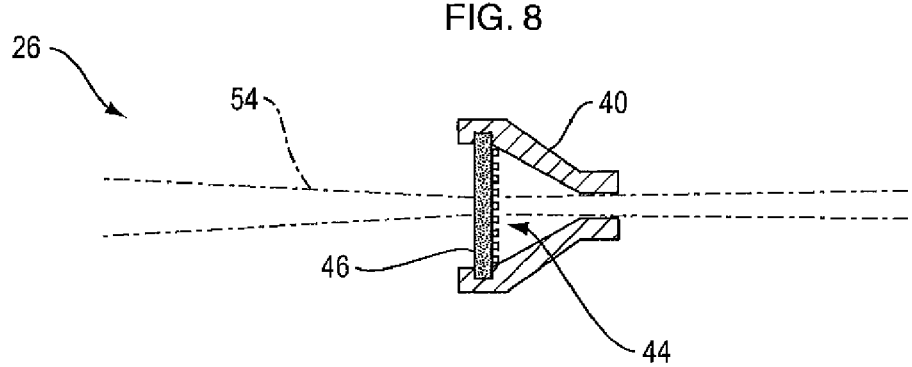
FIG. 9 is a cross sectional side view of the retention device of FIG. 8 with the membrane shown subjected to an IR beam.

In a first embodiment of the retention device 26 represented in FIGS. 8 and 9, the housing 40 is formed into a shape that produces the equivalent effect of the flow expander 50 of FIG. 6. Specifically, the housing 40 includes a gradual tapered section extending away from the location of the support 46 and the membrane 44. The end of the housing 40 is sized to include internal dimensions that substantially match, but slightly exceed, the outer dimension of the terminus of the fluid directing means, such as the end of the syringe 52. In this first alternative embodiment, the retention device 26 may be separated from the fluid directing means, and the entire retention device 26 may be inserted into the analysis subsystem 30 for analysis. FIG. 9 illustrates the complete retention device 26 with the IR beam 54 of an IR spectrometer directed to the membrane 44.

Figure 10:
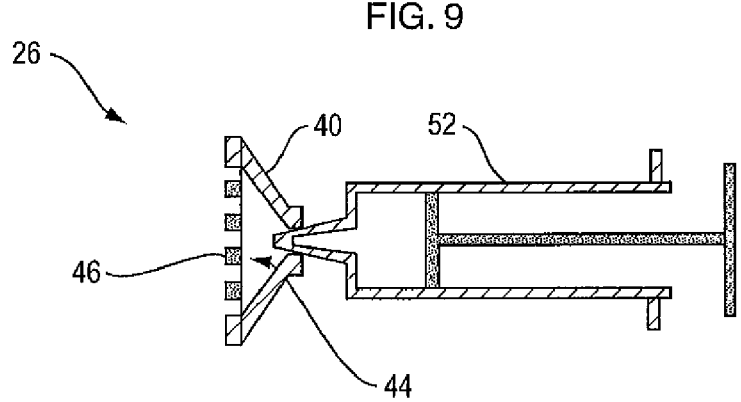
FIG. 10 is a cross sectional view of a second alternative embodiment of the retention device of FIG. 6 in which the support is not a separate unit integrated into the molded device housing, but instead the molded housing itself performs the function of the support.
Figure 11:
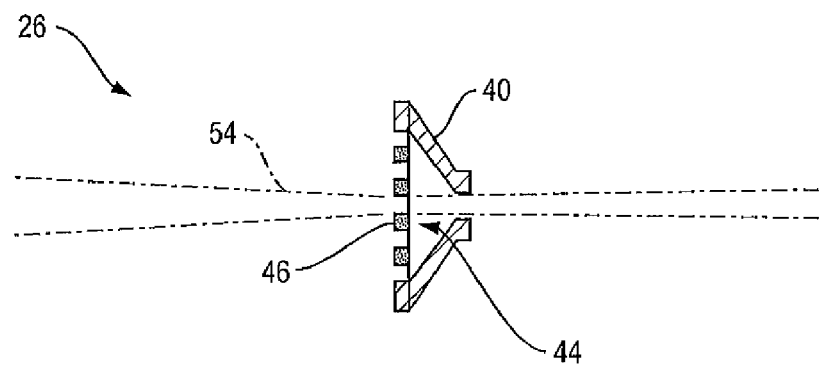
FIG. 11 is a cross sectional side view of the retention device of FIG. 10 with the membrane shown subjected to an IR beam.

In a second embodiment of the retention device 26 represented in FIGS. 10 and 11, the housing 40 is formed into a shape that produces the equivalent effect of the flow expander 50 of FIG. 6. Specifically, the housing 40 includes a sharply tapered section extending away from the location of the support 46 and the membrane 44. The end of the housing 40 is sized to include internal dimensions that substantially match, but slightly exceed, the outer dimension of the terminus of the fluid directing means, such as the end of the syringe 52. In this second alternative embodiment, the retention device 26 may be separated from the fluid directing means, and the entire retention device 26 may be inserted into the analysis subsystem 30 for analysis. FIG. 11 illustrates the complete retention device 26 with the IR beam 54 of an IR spectrometer directed to the membrane 44. It is to be noted that the support 46 shown in FIGS. 10 and 11 is a porous embodiment thereof. As earlier noted, the support 46 may or may not be porous.

Figure 12:
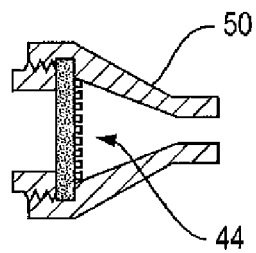
FIG. 12 is a cross sectional side view of the retention device of FIG. 6, showing a portion of the optional flow expander removed
Figure 13:
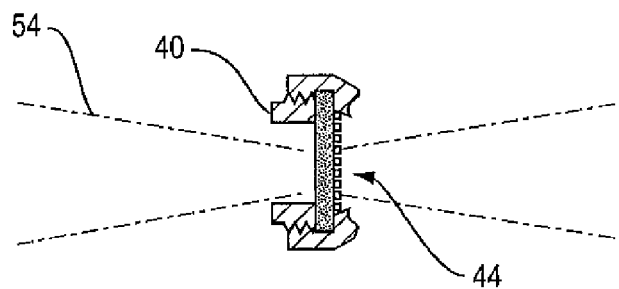
FIG. 13 is a cross sectional side view of the embodiment of the retention device of FIG. 12 with the membrane shown subjected to an IR beam.

FIGS. 12 and 13 illustrate the retention device 26 of FIGS. 6 and 7, in which a portion of the expander 50 may be cut and the remainder left connected to the retention device 26 for insertion in the analysis subsystem 30.

Figure 14:
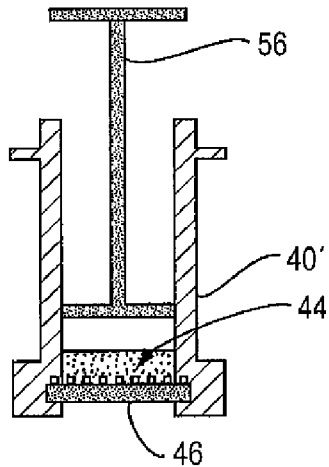
FIG. 14 is a cross sectional elevation view of a third embodiment of the retention device of the present invention.
Figure 15:
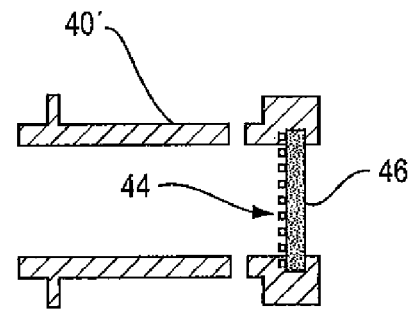
FIG. 15 is a cross sectional side view of the retention device of FIG. 14 with a portion of the housing removed.
Figure 16:
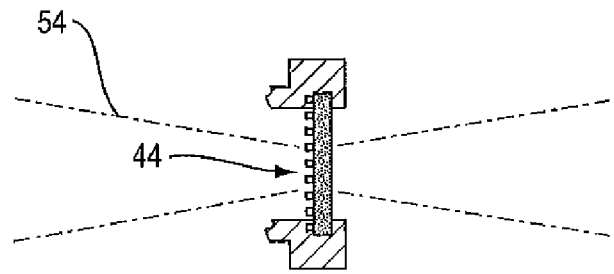
FIG. 16 is a cross sectional side view of the alternative embodiment of FIG. 15 with the membrane shown subjected to an IR beam.

A third embodiment of the retention device 26 of the present invention is illustrated in FIGS. 14-16. In this embodiment, housing 40' forms part of the sample delivery subsystem 24, which may include a piston drive 56 to direct collected sample to the membrane 44 substantially across its entire cross sectional area. In this arrangement, no expander is required to create sample flow uniformity. The housing 40' may be cut, as shown in FIG. 15, such that only a portion containing the membrane 44 forms part of the retention device 26 for transfer to the analysis subsystem 30. The IR beam 54 is then directed to the membrane 44.

Figure 17:
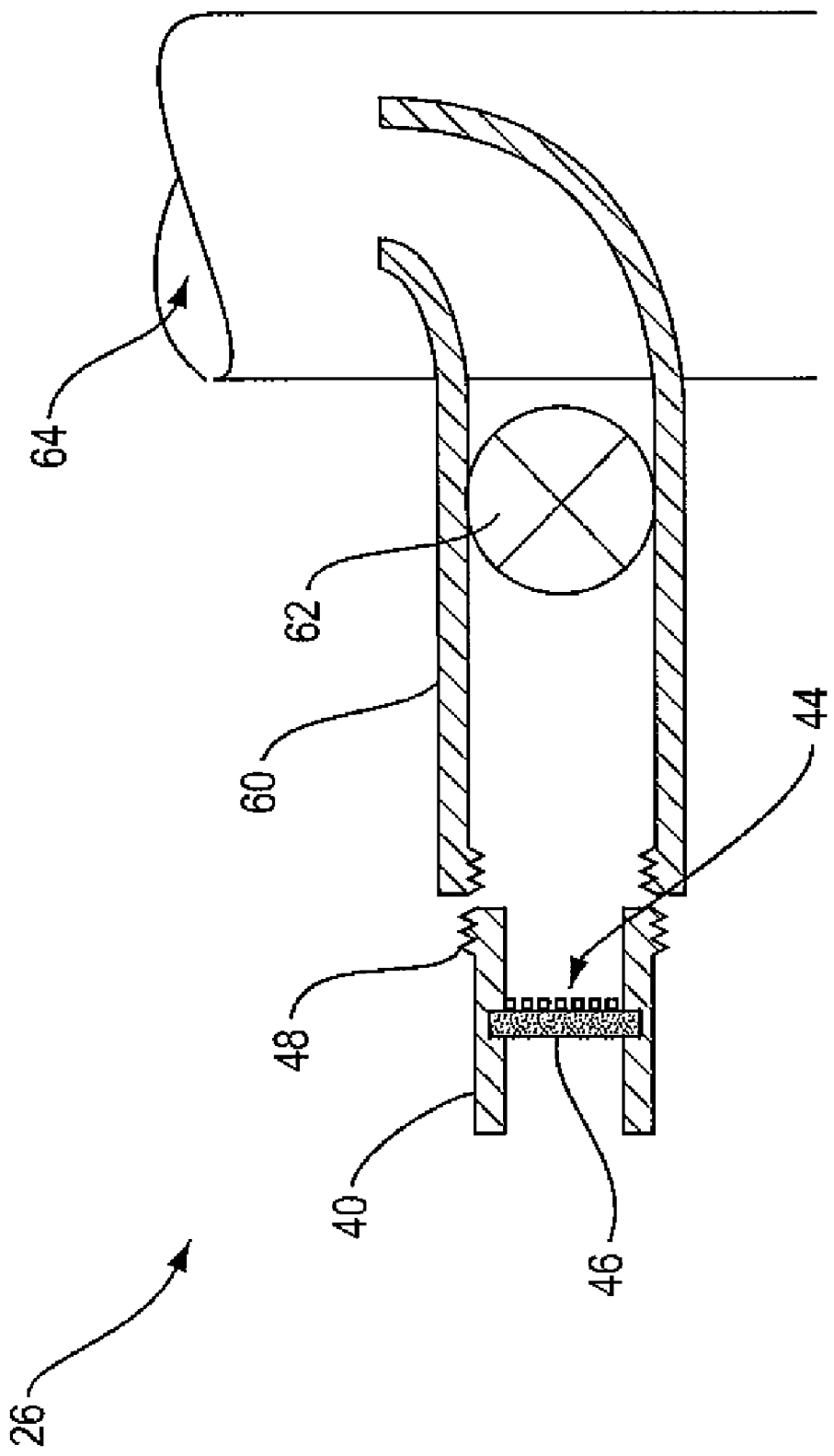
FIG. 17 is a cross sectional side view of another embodiment of the present invention, showing the retention device in proximity to an interface conduit for fluid transfer from a source.

As illustrated in FIG. 17, the retention device 26 including housing 40 with threading 48 may optionally be coupled to an interface conduit 60 with valve 62. The conduit 60 may be joined to a process flow pipe 64 within which a fluid of interest flows. In this arrangement, a sample of the fluid may be collected directly from the process flow pipe 64 without disruption. In addition, samples may be collected when desired and without use of the various collection and transfer steps described herein. A portion of the fluid within the process flow pipe 64 may be selectively directed to the membrane 44 of the retention device 26 by opening the valve 62. That is, the interface conduit 60 may be configured to divert a portion of the fluid toward the retention device 26. The diversion may be achieved with a curved elbow as illustrated, but is not limited thereto. When a sufficient amount of the fluid has passed through or over the membrane 44, the valve 62 may be closed. The retention device 26 may then be disconnected from the interface conduit 60 and treated and/or transferred to the analysis subsystem 30. Those of skill in the art will recognize that other means for establishing a disconnectable interface to a structure where a fluid of interest is located will provide the equivalent opportunity for sample collection on the membrane 44. Further, the retention device 26 could be directly connected to the process flow pipe 64, with the retention device 26 being detachably connectable to the process flow pipe 64. In that arrangement, the flow of the fluid may or may not have to be halted prior to removal of the retention device 26. Moreover, it is to be understood that the process flow pipe 64 is representative of a fluid source and that the present invention is not limited to direct or indirect coupling of the retention device 26 to the fluid source.

Returning to FIG. 1, the optional sample collection and retention device flushing subsystem 27 may be used to ensure that all sample fluid passes through the retention device 26 so that only the analyte remains thereon. It is selected to have at least the following characteristics. It is preferably arranged for adaptation to the sample collection subsystem 18 and the optional sample pretreatment subsystem 22. It is capable of filling the sample collection subsystem 18 with an appropriate fluid (e.g. clean water) to: 1) rinse and flush potentially remaining analyte through the retention device 26; and 2) help optimize the analytical performance of the overall system. The sample collection and retention device flushing subsystem 27 is easily adaptable to sample collection and optional sample pretreatment subsystems via common, inert connections (e.g. LUER connections) that provide unidirectional flow of desired fluid through the retention device 26 during a flushing step, if that optional step is conducted, after analyte sample delivery.

This optional sample collection and retention device flushing subsystem 27 is preferably disposable and/or retained in sterile sealed containment, but need not be. It is a closed system so as to eliminate or minimize the possibility of introducing external contamination into the analysis process. The sample collection and retention device flushing subsystem 27 is fabricated of one or more inert and non-extractable materials; that is, a material(s) that will not leach into the fluid stream during the analysis process. Finally, the sample collection and retention device flushing subsystem 27 may be selected for suitability in an automated operation of a portion or all of the analysis apparatus 10. The three-way valve part no. DCV 115 available from Value Plastics, Inc. of Fort Collins, Colo., connected to a source of appropriate flushing fluid is a suitable embodiment of the optional sample collection and retention device flushing subsystem 27.

Figure 18:
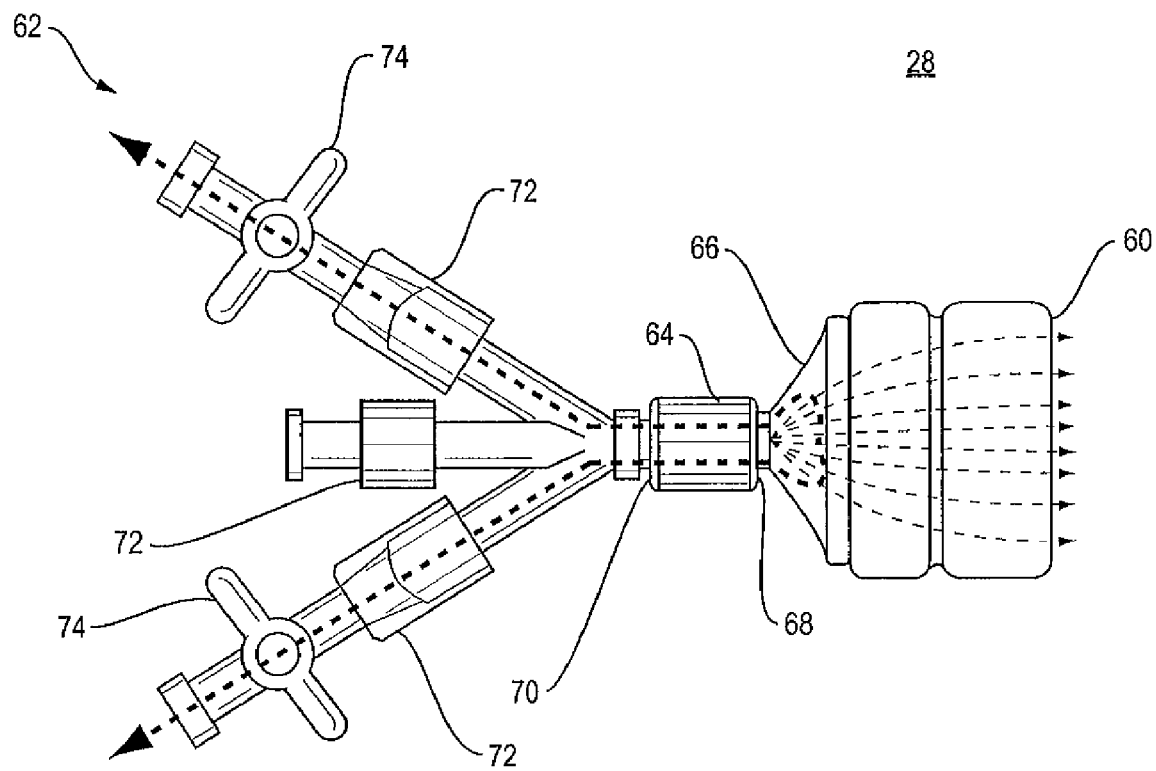
FIG. 18 is a plan view of the drying subsystem including the retention device removably retained therein.
Figure 19:
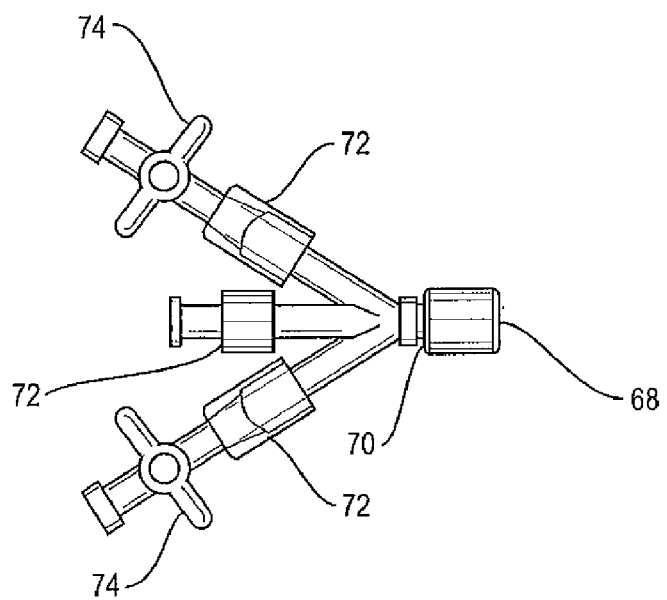
FIG. 19 is a plan view of the manifold of the drying subsystem shown in FIG. 18.

With reference to FIGS. 1, 18 and 19, the drying subsystem 28 is used to remove non-analyte fluid from the retention device 26 prior to conducting the analyte analysis steps of the method of the present invention. The drying subsystem 28 includes housing 60, manifold 62 and interface 64. The housing 60 includes a cavity within which the retention device 26 may be removably affixed. Specifically, the housing 60 includes an inlet 66 that may be configured with a reversibly connector to join to the housing 40 of the retention device 26. For example, each may be threaded. The inlet 66 is further configured for reversible connection to the interface 64 at first interface end 68. The interface is arranged to establish a conduit through which a drying medium, such as air, for example, passes into the housing 60 through the inlet 66. Second interface end 70 of the interface 64 is arranged for reversible connection to the manifold 62. The manifold is arranged with a plurality of drying tubes 72, wherein one or more of the drying tubes 72 may include a valve 74 to enable the user to regulate drying medium flow to the membrane 44 of the retention device 26. For example, the user may wish to open one or more valves partially or completely to generate lateral drying, i.e., drying of the top surface of the membrane 44. Alternatively, the user may wish to close all valves and leave one drying tube 72 open, such as the center one shown in FIG. 17, for the purpose of forcing the drying medium through the membrane 44. Other options for drying orientation, as well as time frames, drying media, and the like will be recognized by those of skill in the art. It is to be understood that the components of the drying subsystem 28 may be fabricated of selectable materials including, but not limited to, nonmetallic materials, provided the materials selected do not adversely impact the intended functionality of the system 10.

It is to be noted that the connection of the drying subsystem 28 to the analyte retention device 26 plays an important role in removing non-analyte fluid/vapors from the membrane 44 and within the housing 40 in preparation for analysis. The drying subsystem 26 is configured to have at least the following characteristics. It is selected to optimize the effect of the drying subsystem 28 to efficiently and effectively dry the analyte retention device 26 prior to analysis without removing retained analyte or introducing interferents or contaminations that would otherwise compromise the analysis process. There may be manual, semi-automated, or automated versions of the drying subsystem 26.

The drying subsystem 26 is designed by encapsulating an input source drying air source internal to a secondary flow dynamics and pressure-controlling assembly. As noted, the manifold 62 is configured to provide the capability to dry the membrane 44 by allowing lateral (across the top of the membrane 44) and/or vertical (through the membrane 44) flow paths and exhaust. The distribution of the lateral and vertical flow amounts can be controlled via the valves 74. The manifold 62 may incorporate automation (e.g. sensors and electronic valves) for feedback and control of the lateral and vertical analyte retention device 26 drying air profile (e.g. time, rate, pressure, lateral/vertical flow distribution).

The drying subsystem 28 may be selected for suitability in an automated operation of a portion or all of the analysis system. Examples of suitable embodiments of the drying subsystem 28 include, but are not limited to, The Norm-Ject syringe from Henke Sass Wolf, any commercially available air pump, such as the Air Pump 7500 made available by Petco Animal Supplies, Inc. of San Diego, Calif., an air compressor, such as the TC-20 Compressor made available by TCP Global of San Diego, Calif. More generally, other means for drying include, but are not limited to, mechanically compressed ambient air, mechanically compressed, dried, and filtered ambient air, and sources of pressurized process gases (e.g. air, nitrogen). As noted, a pressure feedback tool may be employed to observe and regulate the air flow rate of the drying subsystem 28. In addition, a Drierite™ drying tube, such as one available from W. A. Hamilton Co. Ltd. of Xenia, Ohio, may be used to aid in drying the retention device 26.

The analysis subsystem 30 is used to conduct the evaluation of the characteristics of any analytes retained on the analyte retention device 26 after the drying process. The retention device 26 or a portion thereof is either deployed in a test fixture frame or other form of support of the analysis subsystem 30. The analysis subsystem 30 includes at least the characteristics of IR technology (or equivalent). That technology includes radiometric (one small window over the IR spectrum), semi-radiometric (multiple small windows over different regions of the IR spectrum), or full spectrographic depending on application requirements. The analysis subsystem 30 is capable of signal processing for baseline correction, integration, peak height determination and spectral analysis (chemimetrics and/or related statistical processing). It preferably at least includes information storage capacity, one or more libraries of known analyte IR characteristics, a user interface, wired or wireless communication capability, and is capable of receiving and supporting at least the membrane 44 with a scan field similar or less in cross sectional dimensions to the cross sectional dimensions of the membrane 44. It must provide an output of information of sufficient detail to enable one of ordinary skill in the art to be able to make a determination as to the analyte content of the fluid of the gathered sample. The analysis subsystem 30 may be automated and may further be selected for suitability in an automated operation of a portion or all of the complete analysis apparatus 10. Suitable embodiments of the analysis subsystem 30 include, but are not limited to, the MB 3000 FTIR and Horizon software made available by ABB Bomen of Quebec, Canada and the Nicolet iZ10 and the Grams/AI Analysis software made available by ThermoFisher Scientific of Waltham, Mass.

The optional archiving subsystem 32 may be used to store raw and processed information from the analysis process. Its characteristics include, but are not limited to including, sufficient capacity to store electronically any information of interest regarding the sample, analysis and the process. It effectively stores raw and processed information for potential re-analysis. If located in an environment that may be adverse, it is preferably retained in a secure, environmentally conditioned, sealed air- and liquid-tight container. It should be wire or wirelessly couplable to one or more other subsystems of the analysis apparatus 10 in a manner that ensures there is no compromise of the integrity of the apparatus 10 and its sampled result for a determined amount of time (dependent on application). As with the other subsystems, the optional archiving subsystem 32 may be selected for suitability in an automated operation of a portion or all of the complete analysis apparatus 10.

A specific description of the components of the analyte retention device 26 and analysis subsystem 30 follows.

The composition of the membrane 44 of the invention can vary. Certain embodiments include a base material with or without surface treatment. The base material may be nonporous or porous. The pore size may be: 1) in certain embodiments pores less than about 1 mm; 2) in certain embodiments pores less than about 100 µm; 3) in certain embodiments pores less than about 10 µm; 4) in certain embodiments pores less than about 1 µm; and 5) in certain embodiments pores less than about 100 nm.

The base material may be formed of: 1) in certain embodiments metallic materials (including, but not limited to, aluminum, platinum, stainless steel); 2) in certain embodiments semiconductors (including, but not limited to, those based on silicon and germanium); 3) in certain embodiments oxides (including, but not limited to palladium oxide, silicon dioxide, aluminum oxide, and tungsten oxide); and 4) in certain embodiments, a non-metallic material such as a polymeric material including, but not limited to poly(tetrafluoroethylene), polyethylene, polypropylene, and polycarbonate.

The surface treatment, if employed, may be a monolayer or multilayer coating of selectable thickness and material that is either covalently or non-covalently bound. The surface treatment may be applied by any one or more of, but not limited to: 1) in certain embodiments dip coating from solution; 2) in certain embodiments spin casting from solution; 3) in certain embodiments spray coating from solution; 4) in certain embodiments treatment under vacuum; 5) in certain embodiments deposition from supercritical carbon dioxide; 6) in certain embodiments plasma treatment; 7) in certain embodiments chemical vapor deposition; 8) in certain embodiments sublimation; and 9) in certain embodiments evaporation.

The surface treatment material may be formed of, but not limited to, one or more of: 1) in certain embodiments, silanes including, but not limited to, those such as hexamethyldisilazane or 3,3,3-Trifluoropropyl-trichlorosilane; 2) in certain embodiments, metals inclusive of those listed above as possible base materials; 3) in certain embodiments, oxides inclusive of those listed above as possible base materials; 4) in certain embodiments, polymers inclusive of those listed above as possible base materials; and 5) in certain embodiments, small organic molecules including but not limited to anthracene.

The composition of the membrane support 46 can vary. In certain embodiments, the support 46 may be nonporous or porous. When porous, the nominal pore size may be, for example: 1) in certain embodiments pores less than about 3 mm; 2) in certain embodiments pores less than about 1 mm; and 3) in certain embodiments pores less than about 100 µm.

The support 46 may be formed of: 1) in certain embodiments, metallic materials (including, for example, aluminum, platinum, and stainless steel); 2) in certain embodiments, semiconductors (including, for example, silicon and germanium); 3) in certain embodiments, oxides (including, for example, palladium oxide, silicon dioxide, aluminum oxide, and tungsten oxide); and 4) in certain embodiments, a non-metallic material such as a polymeric material including, but not limited to Poly(tetrafluoroethylene), Polyethylene, Polypropylene and Polycarbonate; and may include a coating suitable to improve, for instance, IR-amenability and/or reduce extractable content.

The composition of the housing 40 can vary. In all cases, the housing 40 material should contain experimentally insignificant amounts of extractable content that may interfere with the determination of the amount of analyte present. In the example of hydrocarbon determination, any extractable organic material could interfere with the measurement of the hydrocarbon content. The housing 40 may be formed of: 1) in certain embodiments, metal such as, for example, stainless steel or aluminum; and 2) in certain embodiments, non-metallic material, such as a polymeric material including, but not limited to, the materials, High Density Polyethylene, Low Density Polyethylene, Polypropylene and Polytetrafluoroethylene and may include a coating suitable to improve, for instance, IR-amenability and/or reduce extractable content.

The design of the housing 40 can vary. The housing 40 design: 1) in certain embodiments, provides for fluid flow through the membrane 44; and 2) in certain embodiments, provides for fluid flow across the surface of the membrane 44. In certain embodiments, the housing 40 may be designed to be reusable, i.e. after directing the sample through or across the membrane 44, the housing 40 can be opened, the membrane 44 or membrane 44 and support 46 are removed, and the housing 40 is cleaned for re-use. The housing 40 is re-used by placing a membrane 44 or membrane 44 with support 46 into the housing 40 and closing the housing 40, for example, by connecting threaded pieces together. The housing 40 may be fabricated of: 1) low-extractable plastic, metal, or glass that is manually driven by hand; and 2) in certain embodiments, made from low-extractable plastic, metal, or glass that is driven by a mechanical, electromechanical, or other driving force. The retention device 26 may also include in certain embodiments, a fluid pump such as, but not limited to, a peristaltic pump.

The analysis subsystem 30 includes: 1) in certain embodiments, dispersive spectroscopic devices; 2) in certain embodiments, Fourier Transform spectroscopic devices; 3) in certain embodiments, Attenuated Total Reflectance spectroscopic devices; 4) in certain embodiments, dispersive radiometric devices; 5) in certain embodiments, Attenuated Total Reflectance radiometric devices. The embodiments of the analysis subsystem 30 listed can work by: 1) in certain embodiments, examining the absorbance in the infrared region of the electromagnetic spectrum; 2) in certain embodiments, examining the absorbance in the near-infrared region of the electromagnetic spectrum; 3) in certain embodiments, examining the absorbance in the ultraviolet region of the electromagnetic spectrum; and 4) in certain embodiments, examining the Raman shift spectrum.

EXAMPLE

The invention now being generally described, it will be more readily understood by reference to the following examples, which are included merely for purposes of illustration of certain aspects and embodiments of the present invention, and are not intended to limit the invention.

Example 1

A PTFE membrane of thickness 50 µm, nominal pore size 0.45 µm, and diameter 15 mm was placed over a metal support disk of 0.25 mm pores and 12.7 mm diameter. The excess membrane material was wrapped around to the back of the metal support disk. PTFE washers of 7.1 mm inner diameter, 12.7 mm outer diameter, and 0.75 mm thickness were placed on both sides of the membrane and disk (See FIGS. 4 and 5). Approximately 30 psi. of force is applied by hand to press the washers, membrane and disk together; this is henceforth referred to as the supported membrane unit. The supported membrane unit was placed in a 13 mm infrared window holder (Bruker optics). Transmission Fourier Transform infrared (FTIR) spectroscopy was performed on an ABB FTLA 2000 with a liquid nitrogen cooled mercury-cadmium telluride detector interfaced with a computer. A background spectrum was taken as the average of 50 scans. The supported membrane unit was then placed into a stainless steel filter holder from Advantec (P/N 30100) and tightened by hand to provide water tight seal around the membrane.

Hydrocarbon-in-water test dispersions of concentration 0.1-30 ppm were created by first dissolving hexadecane in methanol and stirring for about 20 min. Hexadecane was used here as a simulant for Oil. A certain amount of the methanol-hexadecane solution was then dispersed into the center of one liter of deionized water as it was being stirred at about 300 rpm by a magnetic stir bar and stir plate. This water-methanol-hexadecane dispersion was then allowed to stir for about 20 minutes to ensure even distribution of hexadecane in water. As all concentrations of hexadecane tested were well above the solubility limit of about 3 ppb in water, the solution existed as a two-liquid-phase system of hexadecane droplets dispersed in deionized water; the size of the droplets was not known.

After the set stir time, about 12 ml of the hexadecane-water dispersion were drawn by hand into a low-extractable plastic syringe. The filter holder containing the supported membrane unit was then attached by LUER-lok to the syringe. The syringe was then placed on a syringe pump set to pump 10 ml in 3 min. When the sample finished flowing, the filter holder was removed from the syringe, the syringe filled with air, the filter holder re-attached to the syringe, and about 10 ml of air forced through the membrane to dry it. This process was repeated two more times to dry the membrane as a large amount of water present on the membrane would interfere with the infrared measurement. The filter holder was then removed from the syringe and opened. The supported membrane unit was removed from the filter holder and again placed into the 13 mm infrared window holder. An FTIR spectrum was taken using the previously-obtained background spectrum, again averaging 50 scans. Five experiments were performed at hexadecane concentrations of 0.1 ppm and 1 ppm; two experiments were performed at hexadecane concentrations of 20 ppm and 30 ppm.

Figure 20A:
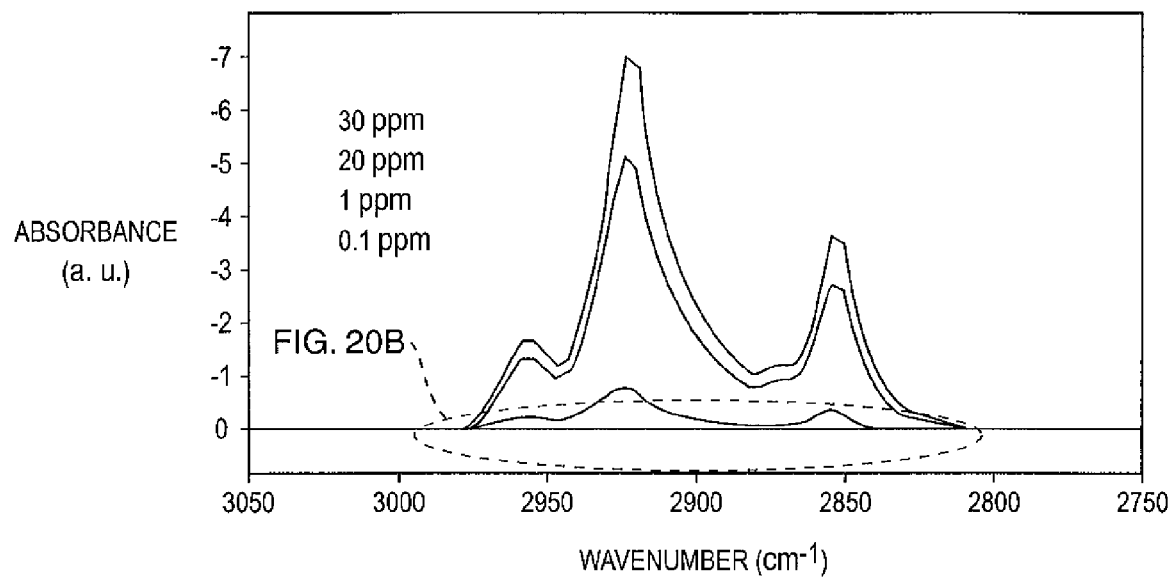
FIGS. 20A and 20B depict FTIR spectra from the results of experiments using one embodiment of the invention. Concentrations of hexadecane in water from 0.1 ppm to 30 ppm were tested.
Figure 20B:
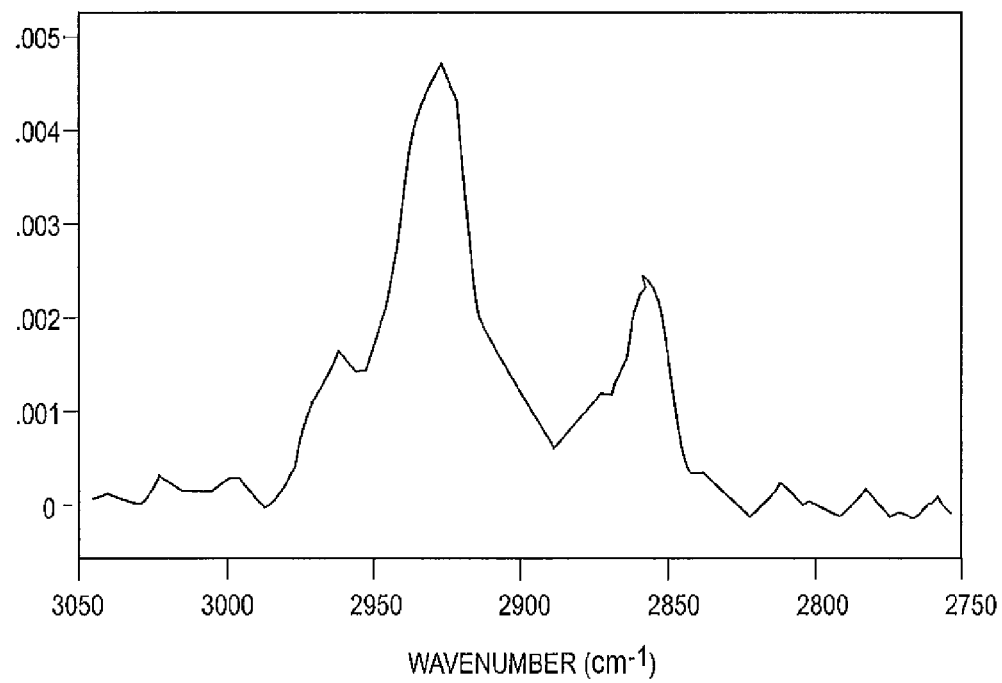

The results of this experimentation are shown in FIGS. 20A and 20B, which show a representative spectrum obtained by testing each of the four concentrations of hexadecane in water. At the high end of 30 ppm hexadecane, the absorbance peaks an easily quantifiable level of about 0.7 absorbance. At the low end of 0.1 ppm hexadecane the peak absorbance is about 0.0045, a level still significantly above the generally accepted minimum signal/noise ratio of 0.001 required for quantification. The peak absorbance can be controlled by syringing different amounts of water and/or using a different membrane area. For instance, the results indicate a concentration of 300 ppm could be tested and still in the quantifiable range by syringing about 1 ml or by expanding the effective membrane area by about 10×. At the low end, the results indicate a concentration of 10 ppb could be tested and quantifiable by syringing about 100 ml or by reducing the effective membrane area by about 10 times.

Example 2

The second example was similar to the first example. A supported membrane unit was made from the same materials, a background spectrum taken, and the same filter holder used in the same way. The only difference was that a 2.3 ppm solution of stearic acid in water was tested. Stearic acid was dissolved in methanol and stirred for 20 min. A certain amount of this solution was then added to 1 liter of deionized water and stirred for 20 min to create an even distribution of stearic acid in water. Stearic acid was used as a simulant for Grease. Grease is included in the TOG definition but not TPH.

Figure 21:
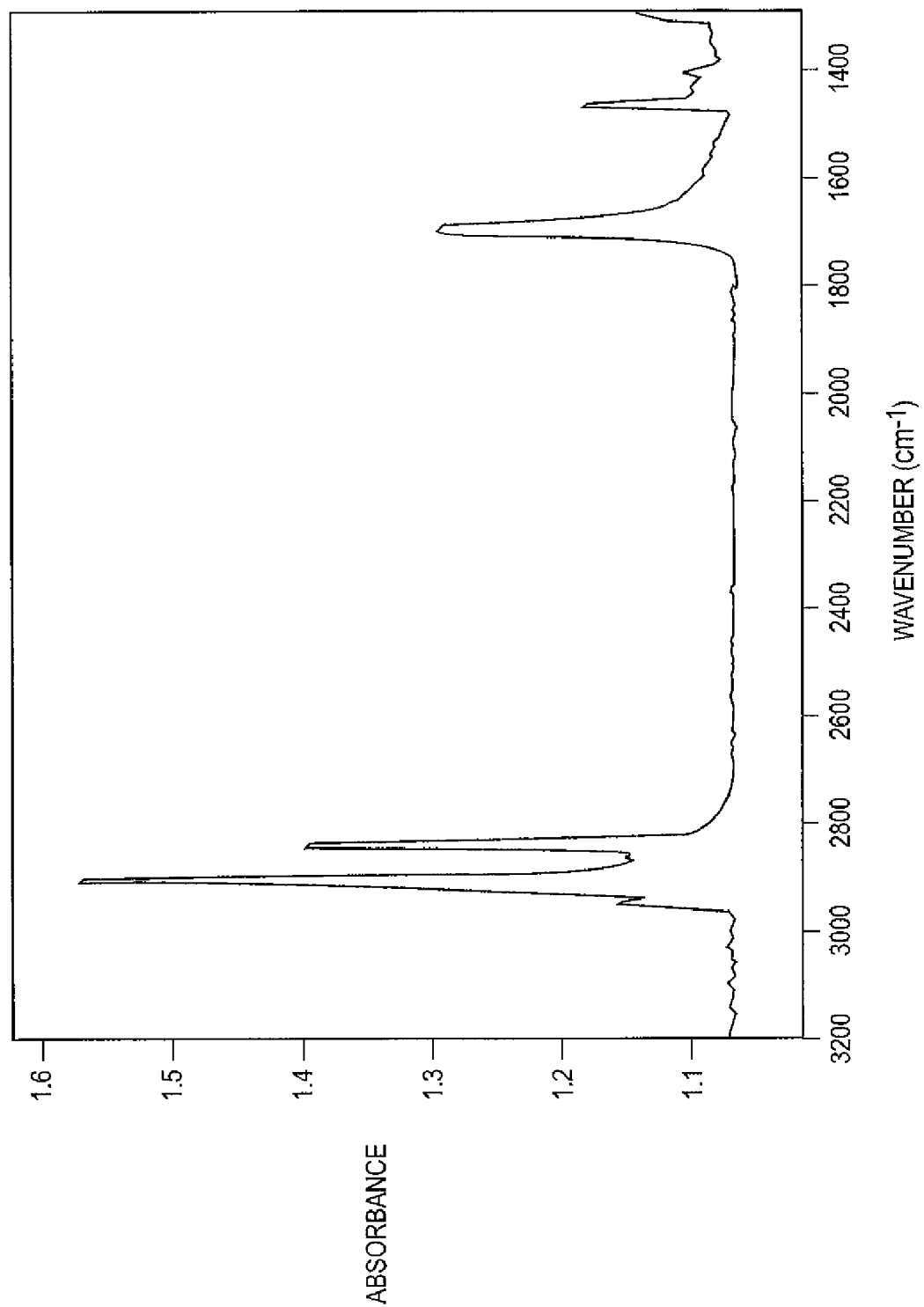
FIG. 21 depicts the FTIR spectrum from the results of an experiment using one embodiment of the invention. A concentration of stearic acid in water at about 2.3 ppm was tested.

The test was performed in the same way as in Example 1. Simply, 10 ml of the stearic acid dispersion in water was syringed through the supported membrane unit and dried in the same manner. However, a small amount of water remained. FIG. 21 shows the results of the test. Stearic acid strongly absorbs at about 1700 cm$^{-1}$, the carboxyl absorbance region, and in the hydrocarbon absorbance region of 2800-3000 cm$^{-1}$. The spectrum shows that Grease can be measured so the invention can be used to determine TOG. However, Grease is an interferent for determining TPH due to the overlapping absorbance in the region 2800-3000 cm$^{-1}$. To address the problem, the absorbance at about 1700 cm$^{-1}$ may be used to determine the amount of Grease present and subtract it from TOG to determine TPH.

Example 3

Figure 22:
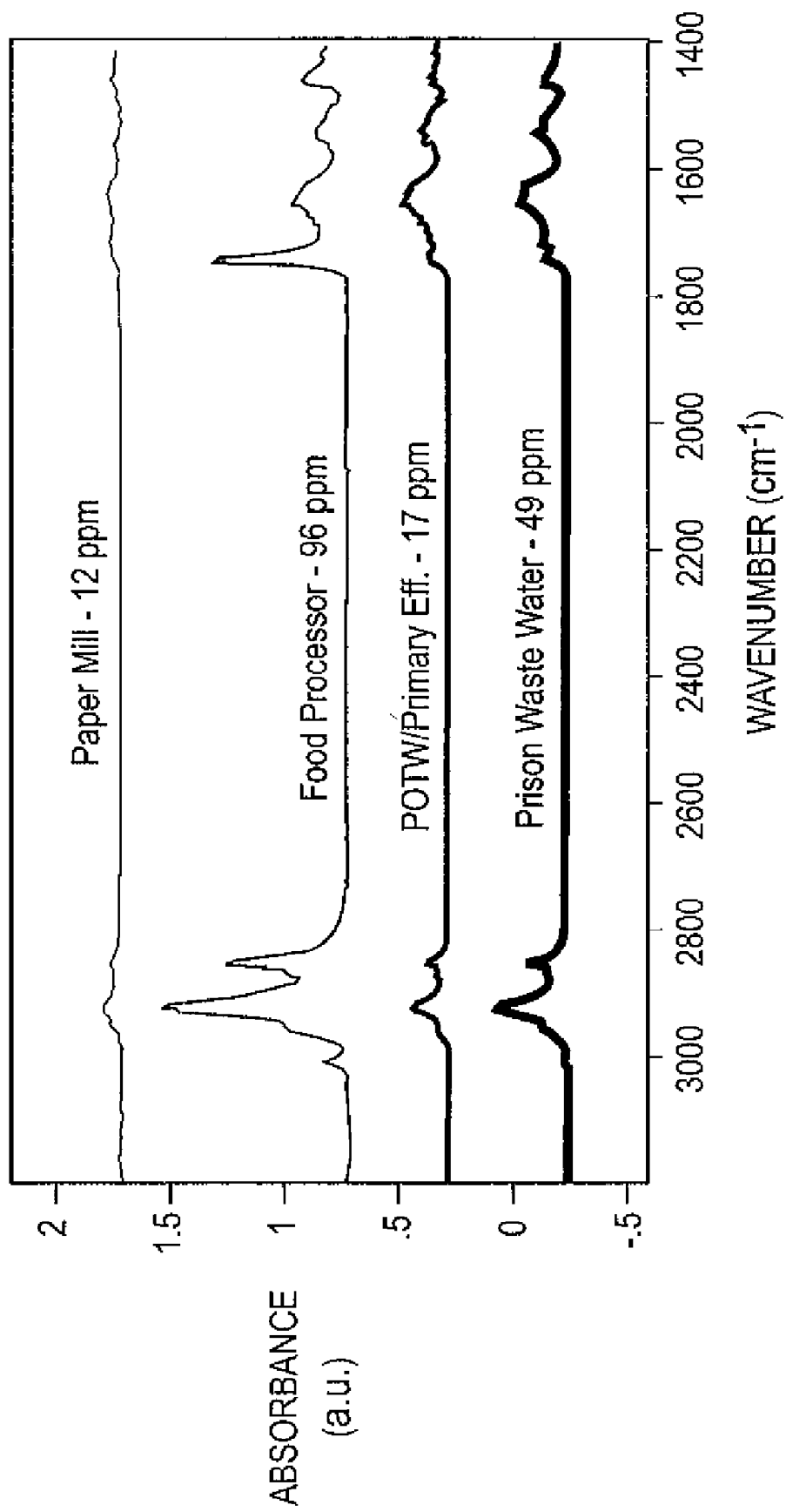
FIG. 22 depicts FTIR spectra from the results of experiments using one embodiment of the invention to examine four samples of real waste water.

The third example is generally similar to the first two in that a supported membrane unit was made from the same materials and a background spectrum taken. However, in this example, six different samples of six different fluids from real-world sources were run through the analysis system of the present invention, three times for each. In addition, a standard solvent-based EPA 1664 analysis was performed on the same fluid samples to determine the relationship between the results obtained using the present invention and the current standard for oil-in-water detection. FIG. 22 shows the spectra resulting from test results for four of the samples (excluding the samples from the Gulf of Mexico). Further, as can be seen from the table of FIG. 23, which identifies the sources of the six samples, the averaged results obtained using the present invention closely matched the results using the conventional solvent-based test method, wherein the conventional solvent-based method is identified as the 1664 Result.

Other variations of the above examples can be implemented. One example variation is that the described method may include additional steps. Further, the order of the steps is not limited to the order illustrated in FIG. 2, as the steps may be performed in other orders, and one or more steps may be performed in series or in parallel to one or more other steps, or parts thereof.

Additionally, certain of the analysis and determination steps of the method and various examples of the analysis performed on the samples collected on the membrane 44 of the retention device 26 and variations of these steps, individually or in combination, may be implemented as a computer program product tangibly as computer-readable signals on a computer-readable medium, for example, a non-volatile recording medium, an integrated circuit memory element, or a combination thereof. Such computer program product may include computer-readable signals tangibly embodied on the computer-readable medium, where such signals define instructions, for example, as part of one or more programs that, as a result of being executed by a computer, instruct the computer to perform one or more processes or acts described herein, and/or various examples, variations and combinations thereof. Such instructions may be written in any of a plurality of programming languages, for example, Java, Visual Basic, C, or C++, Fortran, Pascal, Eiffel, Basic, COBOL, and the like, or any of a variety of combinations thereof The computer-readable medium on which such instructions are stored may reside on one or more of the components of a computing system well known to those of ordinary skill in the art.

A number of examples to help illustrate the invention have been described. Nevertheless, it will be understood that various modifications may be made without departing from the spirit and scope of the invention. Accordingly, other embodiments are within the scope of the claims appended hereto.

What is claimed is:

1. An apparatus for use in the detection of one or more analytes in a fluid, the apparatus comprising:
   a. a membrane formed of one or more materials selected to produce an infrared detectable change thereof as a result of making contact with the one or more analytes, wherein the one or more materials selected exclude any component in sufficient amount to interfere with the infrared detection of the one or more analytes and wherein the membrane is arranged to enable the fluid to pass therethrough;
   b. a housing for holding the membrane; and
   c. a fluid flow connector connectable to a source of the fluid and arranged to direct fluid from the source to the membrane, wherein the fluid flow connector includes a flow expander connectable to the membrane, wherein the flow expander is arranged to receive the fluid from the source and direct the fluid to the membrane in a selectable flow pattern.

2. The apparatus of claim 1 further comprising a membrane support.

3. The apparatus of claim 1 further comprising a surface coating applied to a surface of the membrane.

4. The apparatus of claim 1 wherein the membrane is fabricated to include a base material formed of a metallic material.

5. The apparatus of claim 1 wherein the housing is fabricated of one or more materials selected to exclude any component in sufficient amount to interfere with the infrared detection of the one or more analytes.

6. The apparatus of claim 1 wherein the flow expander is arranged to enable at least a portion thereof to remain connected to the membrane such that the flow expander and the membrane fit into an analyte detection device.

7. The apparatus of claim 1 wherein the source is a process flow conduit and the fluid flow connector is a tap from the process flow conduit.

8. An apparatus for use in the detection of one or more analytes in a fluid, the apparatus comprising:
   a. a detection device capable of optically detecting the one or more analytes;
   b. a fluid flow device for transferring the fluid from a source;
   c. a membrane formed of one or more materials selected to produce an infrared detectable change thereof as a result of making contact with the one or more analytes contained in the fluid when the fluid flow device transfers the fluid to the membrane, wherein the one or more materials selected exclude any component in sufficient amount to interfere with the infrared detection of the one or more analytes;
   d. a housing for holding the membrane in a selectable position in relation to the fluid flow device; and
   e. a fluid flow connector connectable to the fluid flow device and arranged to direct fluid from the source to the membrane, wherein the fluid flow connector includes a flow expander connectable to the membrane, wherein the flow expander is arranged to receive the fluid from the source and direct the fluid to the membrane in a selectable flow pattern.

9. The apparatus of claim 8 further comprising a membrane support for retaining the membrane in the housing, wherein the membrane support is fabricated of one or more materials selected to exclude any component in sufficient amount to interfere with the infrared detection of the one or more analytes.

10. The apparatus of claim 8 wherein the membrane is arranged in relation to the fluid flow device such that the fluid flow device directs the fluid to pass through the membrane.

11. The apparatus of claim 8 wherein the membrane is arranged to enable the fluid to pass over it rather than through it.

12. The apparatus of claim 8 further comprising a surface coating applied to a surface of the membrane.

13. The apparatus of claim 8 wherein the detection device is any one of a spectrometer, a radiometer and a filtometer.

14. The apparatus of claim 2 wherein the membrane support is fabricated of one or more materials selected to exclude any component in sufficient amount to interfere with the infrared detection of the one or more analytes.

15. An apparatus for use in the detection of one or more analytes in a fluid, the apparatus comprising:
   a. a membrane formed of one or more materials selected to produce an infrared detectable change thereof as a result of making contact with the one or more analytes, wherein the one or more materials selected exclude any component in sufficient amount to interfere with the infrared detection of the one or more analytes; and
   b. a fluid flow connector connectable to a source of the fluid and arranged to direct fluid from the source to the membrane wherein the fluid flow connector includes a flow expander connectable to the membrane, wherein the flow expander is arranged to receive the fluid from the source and direct the fluid to the membrane in a selectable flow pattern.

16. The apparatus of claim 15 wherein the membrane is porous.

17. The apparatus of claim 16 wherein the membrane is arranged to enable the fluid to pass therethrough.

18. The apparatus of claim 15 wherein the membrane is arranged to enable the fluid to pass over it rather than through it.

19. The apparatus of claim 15 wherein the membrane is fabricated to include a base material formed of a metallic material.

20. The apparatus of claim 15 wherein the flow expander is arranged to enable at least a portion thereof to remain connected to the membrane such that the flow expander and the membrane fit into an analyte detection device.

21. The apparatus of claim 15 wherein the source is a process flow conduit and the fluid flow connector is a tap from the process flow conduit.

22. The apparatus of claim 15 further comprising a membrane support.

23. An apparatus for use in the detection of one or more analytes in a fluid, the apparatus comprising:
   a. a membrane formed of one or more materials selected to produce an infrared detectable change thereof as a result of making contact with the one or more analytes, wherein the one or more materials selected exclude any component in sufficient amount to interfere with the infrared detection of the one or more analytes;
   b. a membrane support; and c. a fluid flow connector connectable to a source of the fluid and arranged to direct fluid from the source to the membrane, wherein the fluid flow connector includes a flow expander connectable to the membrane, wherein the flow expander is arranged to receive the fluid from the source and direct the fluid to the membrane in a selectable flow pattern.

24. The apparatus of claim 23 wherein the membrane is porous.

25. The apparatus of claim 24 wherein the membrane is arranged to enable the fluid to pass therethrough.

26. The apparatus of claim 23 wherein the membrane is arranged to enable the fluid to pass over it rather than through it.

* * * * *